(12) United States Patent
Nebe et al.

(10) Patent No.: US 6,835,551 B2
(45) Date of Patent: *Dec. 28, 2004

(54) BASOPHIL DEGRANULATION TEST (75) Inventors: Carl Thomas Nebe, Ladenburg (DE); Hartmann Karin, Ellerstadt (DE)

(73) Assignee: Orpegen Pharma GmbH, Heidelberg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 19 days.

(21) Appl. No.: 09/242,114
(22) PCT Filed: Jan. 20, 1997
(86) PCT No.: PCT/EP97/00251
§ 371 (c)(1),
(2), (4) Date: Feb. 10, 1999
(87) PCT Pub. No.: WO98/32014
PCT Pub. Date: Jul. 23, 1998

(65) Prior Publication Data
US 2002/0012955 A1 Jan. 31, 2002

(51) Int. Cl.[7] ............................ C12Q 1/68; G01N 33/53
(52) U.S. Cl. ........................ 435/7.24; 435/6; 435/975; 436/513; 436/800
(58) Field of Search ............................ 435/7.24, 6, 975; 530/388.72, 880.5; 436/513, 800

(56) References Cited

U.S. PATENT DOCUMENTS 4,281,061 A * 7/1981 Zuk et al.
4,436,631 A * 3/1984 Graham, Jr. et al.
4,745,285 A * 5/1988 Recktenwald et al.
5,234,816 A * 8/1993 Terspatten

OTHER PUBLICATIONS

Furuno et al. Biochem and Biophysical Research Communications, 219:740–744, 1996.*
Bernady et al., Revue Francaise d'Allergologie et d'Immunologie Clinique, 36(8):884–888, 1996.*
Brandt et al. J. Immunolog. Methods, 194:95–102, 1996.*
Sainte–Laudy et al., Infla,,. Res. 45: Supplement1:S33–S34, 1996.*
Yanagihara et al. Clin. Exp. Immunol. 108:295–301, 1997.*
Janeway et al. Immunobiology 3rd Edition, Garland Press, pp. 11:10 and Figure 11.5, 1997.*
Current Protocols in Immunology 1991, Coligan et al p. 7.24.3.*
Knol et al. (J. Allergy Clin. Immunol. (1991) 88:328–338,.*
Gane et al. (1995) (Cytometry 19:361–365).*
Lucia et al. (1995)(Cytometry 22:10–15).*
Sainte–Laudy et al. (1994) Aller. Immunol (Paris) 26(6):211–4, Abstract Only.*

* cited by examiner

Primary Examiner—David Saunders
(74) Attorney, Agent, or Firm—Fulbright & Jaworski L.L.P.

(57) ABSTRACT

The present invention concerns a method for determining the degranulation activity of basophilic granulocytes in a sample as well as a reagent kit that is suitable for this. Furthermore the invention also concerns a method for diagnosing allergic hypersensitivity and for monitoring the response to a hyposensitization therapy.

33 Claims, 4 Drawing Sheets

BASOPHIL DEGRANULATION TEST

FIELD OF THE INVENTION

The present invention concerns a method for determining the degranulation activity of basophilic granulocytes in a sample as well as a reagent kit that is suitable for this. In addition the invention also concerns a method for diagnosing allergic hypersensitivity and the response to a hyposensitization.

BACKGROUND AND PRIOR ART

The classical classification of allergies according to Coombs and Gell still largely applies nowadays as a basis for understanding the allergic type 1 reaction of the immediate type and is clearly defined by an IgE-mediated immune response. T cells with a particular cytokine pattern (interleukin 4 and interleukin 5) play a special role in this. As a result B lymphocytes are stimulated to switch to IgE production which only occurs at very low levels in the serum and only develops its fatal effect after cell binding to high affinity receptors and subsequent cell degranulation. The cytokines, in particular interleukin 5, additionally cause an increased maturation of promyelocytes into eosinophilic granulocytes which cause delayed damage especially to the bronchial system by the release of toxic proteins from their granula. The physiological relevance of the type 1 allergy is still completely unclear as well as the reason why the T cells secrete a cytokine pattern for an IgE response.

The determination of specific IgE antibodies in the serum (RAST, CAP etc.) is well established and is especially helpful when known allergens need to be tested or when a skin test is dangerous or technically impossible for example in skin diseases or under the influence of drugs. In these methods the allergens are bound covalently or with high affinity to matrices with a large surface (sponges, beads, paper discs), subsequently incubated with patient serum and then, after washing, a detection is carried out using a radioactive or enzyme-labelled anti-human-IgE antibody. The amount of bound IgE is stated semiquantitatively in so-called RAST and CAP classes or quantitatively in kU IgE/l. The evaluation can be carried out radiometrically (RAST) or for example, fluorimetrically (CAP, enzyme with a fluorogenic substrate).

The advantages of these tests are that they are easy to carry out and there is a good correlation with the gold standard skin test for aeroallergens and so-called atopens. However, serious disadvantages must be accepted. These disadvantages are for example the lack of rare allergens and often epitope changes due to coupling of the allergens to the matrix. In addition a carrier molecule such as human serum albumin is required for smaller allergens (haptens). Further difficulties are caused by the fact that the specificities of serum IgE and membrane-bound IgE on basophils and mast cells are not necessarily the same since only a slow exchange takes place. Also the threshold of degranulation readiness (releasability) is not detected. Correlation with the response to a hyposensitization in the form of an IgE decrease is only fairly satisfactory for insect venom allergens i.e. in the majority of cases there is no explanation. Furthermore the specific IgE values must be put into perspective in the case of atopic patients with a high IgE level i.e. the total IgE level of the patient must be known. The severity of the clinical picture hardly correlates with the level of the specific IgE concentration.

Ready-made test strips have been developed as a simplified version of this method on which the various allergens are applied. They are evaluated by comparing the blue colour that forms with a colour scale. Inhalation antigens which produce a reaction in the higher RAST classes are readily detected. Otherwise there is little comparative data. The test is primarily conceived for allergists in private practice who do not have a large laboratory.

Due to the problems mentioned above in determining specific serum IgE, tests have been developed in which the basophilic granulocytes are degranulated after stimulation with an allergen and subsequently the released components of the granula are determined in the supernatant. Such components are for example histamine (Immunotech Co. IBL), leukotrienes (CAST-ELISA, Biermann Co.) or tryptase (Pharmacia Co.). These assays are designed as enzyme immunoassays in a batch procedure and require a duration of two days due to overnight incubation steps. A further disadvantage with regard to the histamine determination is the acylation step for the released histamine as well as a frequently excessively high histamine content of the allergen solutions due to bacterial contaminations. Furthermore for economic reasons it is necessary to collect the supernatants of several patients which delays the assessment. The degranulation must, however, be carried out on fresh whole blood on the day of blood withdrawal.

Therefore attempts have already been made to detect the degranulation cytometrically. In one approach the absorption of basophilic granula was determined with a Technicon H6000 measuring instrument. In this case the measurement points were counted by hand on the screen (Nilsson, Eur. J. Haematol, 45 suppl 53, 50–54, 1990). Alternatively the axial loss of light is measured after staining with toluidine blue in an Ortho cytofluorograph (Nakagawa et al. (Allergy 36, 39–47, 1981). A further approach is to carry out a flow-cytometric two colour immunofluorescence method in which differently labelled anti-CD45 and anti-IgE antibodies are used (Gane et al., Cytometry 19, 361–365, 1995). This method is based on a relative increase of the expression density of CD45 and a reduction of the IgE antibody expression in degranulation. However, a disadvantage of this method is that the change in the CD45 expression density is only small.

None of these cytometric methods has been introduced for routine use due to the said disadvantages since they are tied to special, not generally available instruments or the signal differences are very slight. Furthermore it is difficult to measure the basophils since they are rare in the blood and are very difficult to distinguish from other leucocytes on the basis of scattered light properties alone.

SUMMARY OF THE INVENTION

Hence the object that forms the basis of the present invention is to provide a new method for determining the degranulation activity of basophilic granulocytes which can be carried out simply and rapidly and can be performed with conventional flow cytometers which are widely used in hospitals and laboratory practices.

DETAILED DESCRIPTION OF PREFERRED EMBODIMENTS

This object is achieved by a method for determining the degranulation activity of basophilic granulocytes in a sample, wherein a) the sample is mixed and incubated with a test substance, b) the sample is mixed and incubated with a first binding molecule which can bind to cell-bound IgE antibodies or high affinity receptors thereof, and with a second binding molecule which can bind to a surface molecule which appears de novo on the surface of basophilic granulocytes during degranulation, in which the first binding molecule and the second binding molecule carry different marker groups that can be detected concurrently or can each bind to different marker groups that can be detected concurrently, and c) the labels of the binding molecules are determined separately and the degranulation activity in the sample is determined qualitatively or/and quantitatively on the basis of this determination.

In the method according to the invention the basophils are firstly unequivocally determined via the marker using a first specific binding molecule e.g. an antibody. This first binding molecule binds to cell-bound IgE antibodies or high affinity receptors thereof. Only basophils have a high surface density of IgE molecules which are bound to high affinity receptors ($Fc_eR1$). IgE-specific or receptor-specific antibodies are preferably used which do not lead to a cross-linking of the IgE.

A further special feature of the method according to the invention is that a second binding molecule is used which can bind to an antigen that only appears on the surface as a result of degranulation (de novo expression). An example of such an antigen is the preformed lysosomal protein gp55 which does not appear on the surface until the granula membrane has fused with the cytoplasmic membrane during degranulation and can be detected there.

The term "test substance" in the present invention is understood as any molecule which can cause an activation of basophilic granulocytes or degranulation. The test substance is usually an allergen such as plant pollens, an insect venom such as bee or wasp venom, a drug such as penicillin or a latex allergen. In addition "test substance" also refers to other biological and synthetic substances which can cause such an activation and can be used in the sense of a positive control. An example of this is the chemotactic peptide fMLP.

In one embodiment of the method according to the invention the sample is preincubated with a stimulant such as a cytokine which amplifies the degranulation activity. The amount of cytokine is preferably 0.1–100 ng per test mixture. This preincubation leads to a sensitization of the basophilic granulocytes which reduces the threshold for degranulation readiness (releasability). The stimulant used is preferably a lymphokine such as an interleukin or a growth factor such as a colony stimulating factor (CSF). IL-3 or GM-CSF are preferred. Preincubation with the cytokine is usually carried out before step (a) of the method according to the invention i.e. before adding the allergen, but it can also be carried out simultaneously with the allergen incubation.

Incubation with an allergen as the test substance in the case of a sample derived from an allergy patient leads to an activation of the basophilic granulocytes and thus to a degranulation the extent of which correlates with the extent of the allergic reaction. The first binding molecule serves to define the basophilic granulocytes and the second binding molecule serves to define that portion of the basophilic granulocytes in which a degranulation has taken place. The relative proportion of the degranulated granulocytes can thus be determined in a simple manner from the ratio between the cells that are positive for the first and second binding molecule and the cells which are only positive for the first binding molecule.

The antigen recognized by the second binding molecule is usually a protein or a glycoprotein which only appears on the surface as a result of degranulation and thus allows an unequivocal differentiation between degranulated and non-degranulated granulocytes. The surface molecule is preferably gp55.

Any biological substances can be used as the first and second binding molecule provided they bind specifically either to IgE antibodies or to their high affinity receptors or to a degranulation-specific surface molecule. An antibody or an antibody fragment is preferably used as a first or/and a second binding molecule. Monoclonal antibodies are preferred but polyclonal antibodies are also suitable. In particular for the first binding molecule, those antibodies or antibody fragments are suitable which have a high specificity but low cross-linking or degranulation properties (e.g. Fab fragments). Antibodies or antibody fragments against the $Fc_e$ receptor are particularly suitable as the first binding molecule since the cells in only a small number of the patients are inadequately recognized and activated by anti-IgE.

Furthermore it is preferred in the method according to the invention to terminate the degranulation after a defined incubation period with the allergen and the first and second binding molecule. This can for example be achieved by fixing the leukocytes. Furthermore it is preferable to lyse the erythrocytes after the incubation. Lysis of the erythrocytes and fixing of the leukocytes can also optionally be carried out in one step. Hence a solution is added to the sample which for example contains a high concentration of ammonium chloride and EDTA. Solutions which contain formaldehyde and/or ethylene glycol are also suitable. A preferred solution for carrying out lysis and fixation is a commercially available solution under the trade name FACS lysing solution (Becton Dickinson). A wash step is optionally carried out after the fixation.

In addition to the determination of IgE and de novo expressed surface molecules, the method according to the invention can also comprise the determination of one or several additional parameters. Thus the sample can be additionally incubated with a third binding molecule which is capable of binding to the surface molecule CD45 and carries a marker group or is capable of binding to a marker group which can be determined separately in addition to the marker groups of the first and second binding molecule. The third binding molecule is preferably an anti-CD45 antibody or a fragment of such an antibody.

The additional determination of CD45 whose expression is increased after activation of the basophilic granulocytes further increases the accuracy of the determination.

A further parameter that can also be determined in the method according to the invention is the light that is scattered sideways which increases during degranulation of basophils.

The binding molecules used in the method according to the invention can carry a marker group or can bind to a marker group. If the binding molecule carries a marker group i.e. is directly labelled, it is preferably present as a covalent conjugate with the marker group. On the other hand the binding molecule can also be indirectly labelled i.e. it does not directly carry a detectable marker group but can bind to a further substance which carries the marker group. Examples of indirectly labelled binding molecules are hapten-coupled antibodies which can bind to an anti-hapten antibody carrying a marker group. The coupling of marker groups and haptens to biological binding molecules, in particular to antibodies or antibody fragments, is known to a person skilled in the field of immunological test procedures and does not therefore require further elucidation. Directly labelled binding molecules are preferred for the method according to the invention.

Essentially all known markers in the field of diagnostic detection methods are suitable as marker groups for the binding molecules, where the only prerequisite is that the individual markers can be determined concurrently. Fluorescent markers are preferred which each have a different spectral emission spectrum e.g. fluorescein, phycoerythrin (PE) and peridinium-chlorophyll-A protein (Per CP) or a PE-cyanine 5 tandem conjugate (e.g. cychrome). The determination is preferably carried out in a flow cytometer.

According to another preferred embodiment of the present method a DNA dye which can be determined in addition to the marker on the anti-IgE antibody and receptor is added and determined as a further parameter. The DNA dye serves to stain the cell nuclei and thus to exclude thrombocytes and unlysed erythrocytes. A fluorescent dye such as 7-aminoactinomycin D or propidium iodide is preferred. 7-aminoactinomycin D is particularly preferred.

The sample used in the method according to the invention is a body fluid which contains granulocytes. A particular advantage is that the method according to the invention can be used on whole blood without requiring a cell isolation of basophilic granulocytes. Heparinized whole blood is preferred as the sample and it is generally derived from a human donor although other samples from mammals such as rodents can also be used.

The method according to the invention is very simple and rapid. It can be carried out on any commercial flow cytometer which are present in all medium and large hospitals and laboratories.

The method conditions can be varied depending on the test format used. When using fluorescent markers and a flow cytometric detection of the markers, suitable conditions for step (a) i.e. incubation with the test substance have turned out to be a time period of 5 to 60 min, preferably of 20 to 40 min at a temperature of 25 to 40° C., preferably of 35 to 39° C. A 30 min incubation at about 37° C. gives good results. Step (b) is preferably carried out in the cold in order to avoid unspecific degranulation and suitable conditions have turned out to be a temperature of 0 to 10° C., preferably a temperature of 0 to 5° C. for a time period of 10 to 40 minutes, preferably of 5 to 30 minutes. If a fixation is carried out after step (b), a further cooling of the sample is not essential since the fixation prevents further degranulation. Step (c), i.e. the determination of the markers, is carried out following the incubations and optionally lysis and subsequent wash steps. In this connection the measurement sample is adequately stable for a period of at least one hour, preferably about two hours or more.

As is apparent to a person skilled in the art, it is expedient to measure suitable controls in a determination by the inventive method in which a mixture without the test substance is suitable as the negative control and a substance that activates the granulocytes such as fMLP is suitable as a positive control. Furthermore it is advantageous to also measure a sample whose values are essentially in the normal range such as a body fluid from a healthy normal test person.

A further subject matter of the present invention is a reagent kit for the determination of the degranulation activity of basophilic granulocytes in a sample. The reagent kit contains a first binding molecule which can bind to cell-bound IgE antibodies or their high affinity receptors and a second binding molecule which can bind to a surface molecule which appears de novo on the surface of basophilic granulocytes during degranulation in which the first and the second binding molecule carry different marker groups that can be detected concurrently or each can bind to different marker groups that can be detected concurrently. Optionally the reagent kit can contain a third binding molecule as an additional detection reagent which can for example bind to the CD45 surface molecule and carries a marker group which can be detected in addition to the markers of the first and second binding molecule or can bind to such a marker group. The reagent kit can also contain a DNA dye. Further optional components of the reagent kit are test substances i.e. various allergens or positive control substances such as fMLP. In addition the reagent kit can also contain stimulants such as cytokines or/and reagents for lysing erythrocytes or/and for fixing leukocytes.

Furthermore the kit can additionally contain a reagent for lysing erythrocytes and/or for fixing leukocytes as well as optionally conventional buffers, auxiliary substances or additives.

A preferred reagent kit contains for example at least one test substance, an anti-gp55-FITC antibody, an anti IgE-PE antibody, a FACS lysing solution as well as optionally 7-aminoactinomycin D or/and an anti-CD45-PerCP antibody and a stimulant such as IL-3 or GM-CSF.

Yet a further subject matter of the invention is a method for diagnosing the allergic hypersensitivity of a patient or the response to a hyposensitization which is characterized in that the degranulation activity of basophilic granulocytes is determined in a sample from a patient by means of the method according to the invention using one or several allergens and a positive control as test substances, the degranulation activity in a negative control sample is determined in an additional test mixture and the presence or the absence of an allergic hypersensitivity or the success or failure of a hyposensitization therapy is determined by comparing the values that are obtained.

An appropriate negative control sample is a sample from the same patient to which no test substance has been added in step (a) of the method according to the invention and preferably a stimulated sample of a healthy normal test person is also assayed as a second negative control sample.

An additional subject matter of the invention is the use of anti-gp55 antibodies in a method for determining the degranulation activity of basophilic granulocytes and the use of the method and reagent kit according to the invention for the diagnosis of allergic hypersensitivity and for monitoring the response to a hyposensitization therapy.

EXAMPLE 1

Peripheral blood (heparinised) of the patient is incubated with various concentrations of the suspected allergen at 37° C. In the case of a corresponding sensitization this leads to a degranulation of the basophilic granulocytes and to an activation which is primarily characterized by expression of the gp-55 antigen. In addition the expression density of the IgE receptor decreases and the density of CD45 on basophils increases. The side scattered light increases (loss of absorbing granula) and the number of basophils in the scattered light gate for lymphocytes decreases. The detection is carried out by a three colour immunofluorescence and flow cytometric analysis. The chemotactic peptide fMLP serves as a positive control and a buffer solution (PBS) is used as the negative control. Antihistamine administration inhibits the test.

1. Material 1.1 Reagents

Sheath liquid: FACS-flow (Becton Dickinson Co. order No. 342003) or another carrier liquid with a low intrinsic fluorescence.

FACS lysing solution, 10× concentrate (Becton Dickinson Co. order No. 349202).

Wash solution: PBS (phosphate buffered saline without calcium and magnesium) as a ready-to-use solution or as salts (e.g. Biochrom, Berlin) or PHAGO-BURST wash solution (ORPEGEN Pharma Co., Heidelberg).

Chemotactic Peptide fMLP (2000×) (ORPEGEN Co.) diluted in PBS.

For the calibration of quantitative measurements: Calibrite calibration particles, Becton Dickinson, order No. 349502.

1.2 Monoclonal Antibodies a) anti gp55-FITC, (ORPEGEN Pharma), order No. 1464 (prediluted 1:4 in the ready-made combination)

b) anti IgE-PE (ORPEGEN Pharma), order No. 1465 (prediluted 1:40 in the ready-made combination)

c) anti CD45 PerCP (Becton Dickinson) or CD45 cychrome (Pharmingen), order No.

1.3 Allergens

ALK depot SQ (Scherax) mixture of 6 grasses+rye 100,000 U/ml, order No. 145a/90.90c latex allergen (ALYOSTAL ST-IR) order No. 0903

ALK-prick SQ (Scherax) bee venom, order No. 222a/85a, 300 µg/ml

ALK-prick SQ (Scherax) wasp venom, order No. 223a/85a, 300 µg/ml

Allergopen (penicillin G, PPL and derivative MDM), order no. 162a/81, penicillin "Grünenthal" 1 mega, PZN-7803133 mite allergen from the Geer Labs company among others.

2. Procedure 2.1 Sample Preparation

The sample to be examined is divided into aliquots of 100 µl in each case. In the case of high leukocyte numbers (WBC of 10–20,000 C/µl) it is possible to use a smaller sample volume e.g. 50 µl. Multiple test mixtures are not necessary.

2.2 Preparation of the Allergen Dilutions

ALK-depot SQ (Scherax) mixture of 6 grasses+rye is used at concentrations of 10,000, 1,000, 100 and 10 U/ml. ALK-prick SQ (Scherax) bee venom and ALK-prick SQ (Scherax) wasp venom are used at concentrations of 10, 1, 0.1 and 0.01 µg/ml. Latex allergens, PPL (allergopen) and MDM (allergopen) are used in dilutions of 1:10, 1:100 and 1:1,000. Penicillin Grünenthal is used at concentrations of 100, 10, 1 and 0.1 µg/ml. PBS serves as a negative control and fMLP at a concentration of $10^{-7}$ M (i.e. 1:2,000 PBS) is used as the positive control. A sample from a healthy normal test person is also assayed as a further control.

2.3 Incubation with Allergen

100 µl of each of the allergen dilutions is added to an aliquot of the sample, mixed and incubated for 30 minutes at 37° C. in a water bath. Then the mixtures are placed on ice.

2.4 Addition of Antibodies

The following antibody solutions are then added.

a) 20 µl anti gp55-FITC (prediluted)

b) 20 µl anti IgE-PE (prediluted)

c) 10 µl anti CD45-cychrome or 20 µl CD45-PerCP

After antibody addition it is well mixed (vortex) and incubated for 20 minutes on ice while protected from light.

2.5 Lysis and Fixing 2 ml FACS lysing solution (erythrocyte lysis and leukocyte fixation) is then added, it is mixed (vortex) and incubated for 10 minutes at room temperature while protected from light. Subsequently it is centrifuged for 5 min at 1300 rpm or 300 g and decanted.

2.6 Washing the Cells

The cells are washed by adding 3 ml wash solution (PBS), centrifuging (5 min at 1300 rpm or 300 g) and decanting.

2.7 Measurement

The sample is measured by flow cytometry for example on an FACS scan instrument. The stability of the measured sample is presumably $\geq 2$ hours on flaked ice in the dark.

The instrument settings ("BASO-SET" in the program CellQuest®) can be selected as follows.

| Parameter | Amplifier | Expected value | resolution |
|---|---|---|---|
| FSC | lin | E00 (2.0) | 256 channels |
| SSC | lin | 360 | 256 channels |
| FL1 | log, 4 decades | 620 | 256 channels |
| FL2 | log, 4 decades | 500 | 256 channels |
| FL3 | log, 4 decades | 620 | 256 channels |
| trigger on FSC | | 100 | |
| compensation | FL1-% FL2 | 0.9 | |
| | FL2-% FL1 | 21 | |
| | FL2-% FL3 | 0.2 | |
| | FL3-% FL2 | 29 | | filter combinations (not variable in the FACScan):

| Parameter | spectrum | fluorochrome | filter |
|---|---|---|---|
| FL1 fluorescence 1 | green fluorescence | FITC, TO | BP530 +/− 15 nm |
| FL2 fluorescence 2 | orange fluorescence | PE, PI | BP585 +/− 22 nm |
| FL3 fluorescence 3 | red fluorescence | PerCP, red613, Cy5, PI | LP > 650 nm |

In the SSC/IgE dot plot, a region is set around the cells with low and high side scattered light and strong IgE expression. These cells are optionally displayed in the dot plot FL3 (CD45) versus FL2 (IgE) as part of the validation and the x and y mean values of this population are evaluated and the FL1 histogram (gp 55). The markers are set such that the evaluation region covers the region of the gp55 positive basophils (the PBS test mixture serves as a negative control). The mean value FL1 is observed in all (also gp55-negative) cell populations. If possible, at least 1000 cells of the subclass of interest (in this case basophils) are recorded. In the positive test mixture a bimodal distribution is formed in which the activated basophilic granulocytes represent an individual population. It is therefore possible to view the percentage which is adequate for evaluating the test result.

3. Evaluation

Figure 1:
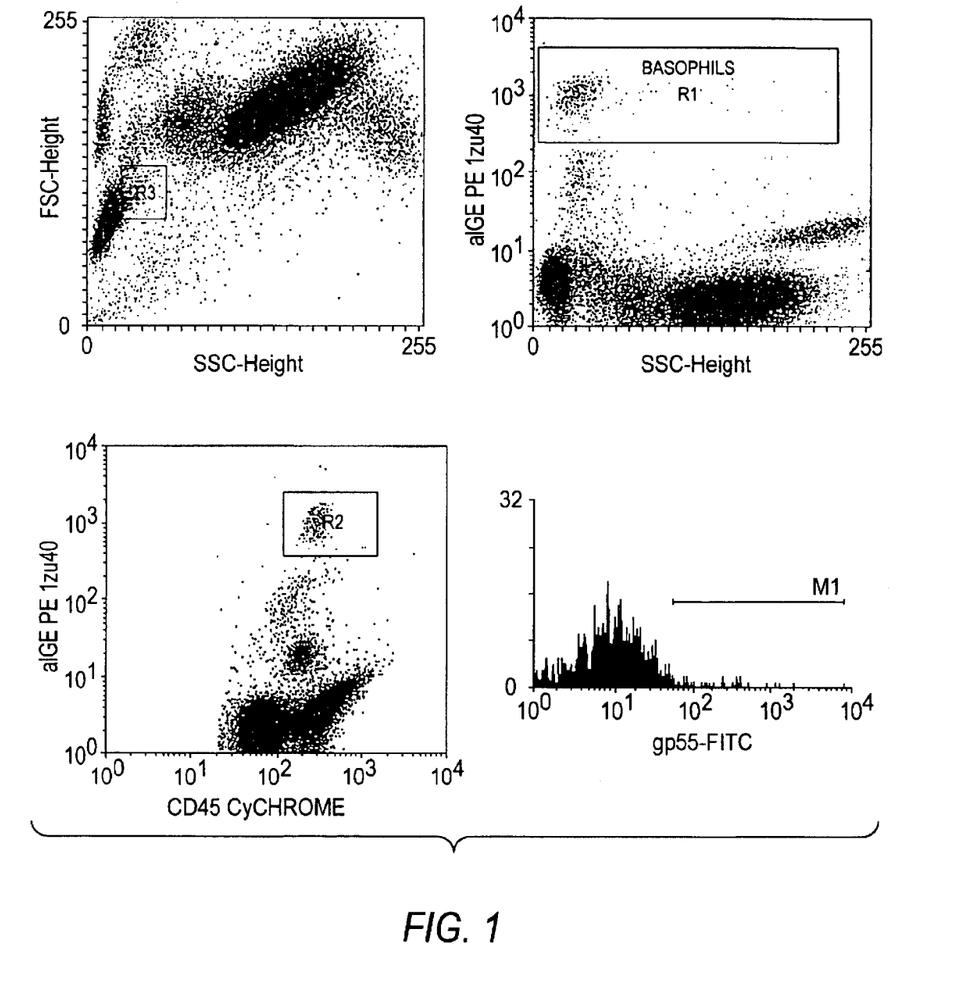
FIG. 1 shows the evaluation of a test control according to the invention for a negative control
Figure 2:
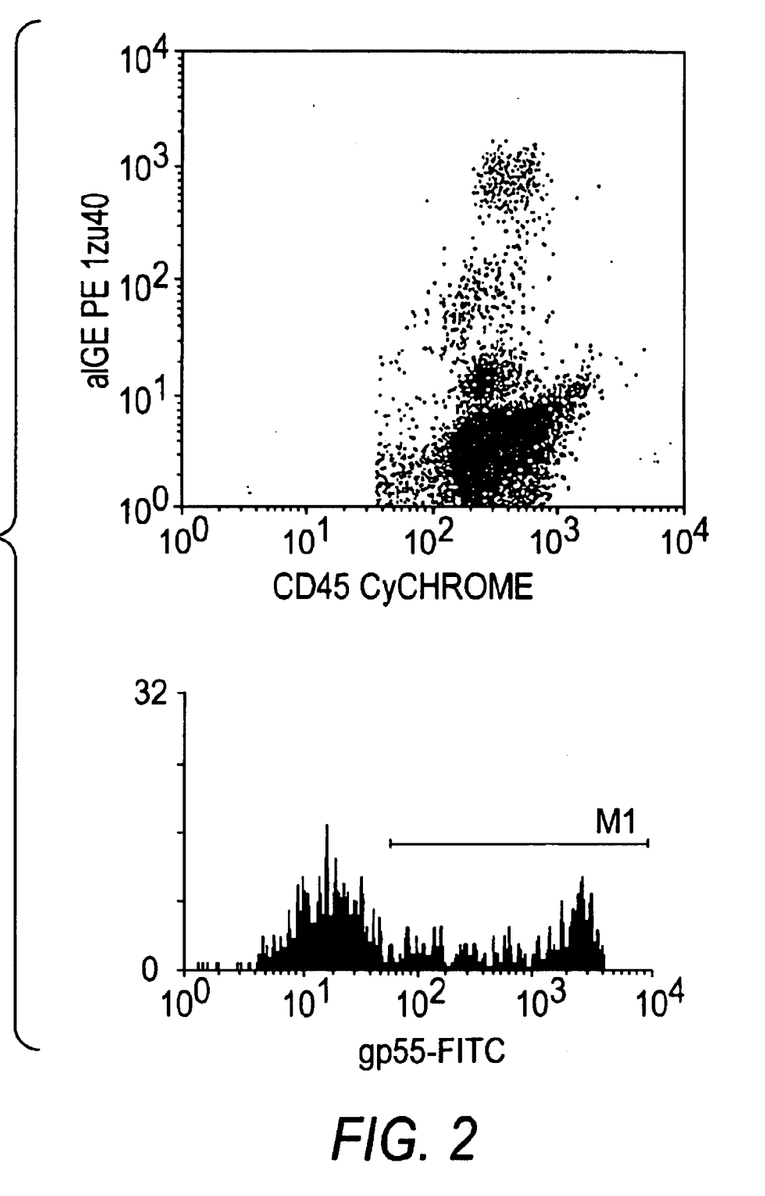
FIG. 2 shows the evaluation of a test according to the invention for a positive control FIGS. 3–5, inclusive, show comparison of tests according to the invention, with a histamine release test of prior art.

The evaluation of a negative control containing PBS is shown in FIG. 1. The evaluation of a positive control containing fMLP is shown in FIG. 2.

The following Table 1 shows typical values where all parameters should be taken into consideration as a plausibility check. A comparison between the negative control (PBS) and positive control (fMLP) shows that the percentage of basophils remains essentially constant, the CD45 expression density increases after activation and the IgE density decreases slightly. The percentage of gp55-positive basophilic granulocytes and the mean gp55 value increases strongly after activation.

| assay | % basos | mean CD45 | mean IgE | % gp55 | mean gp55 |
|-------|---------|-----------|----------|--------|-----------|
| PBS   | 2.50    | 134       | 1032     | 3.3    | 33        |
| fMLP  | 2.35    | 349       | 981      | 30.6   | 369       |

A comparison of the diagrams for CD45 and gp55 for the positive and negative control shows that a considerably higher allergen-specifically induced increase of expression occurs in the case of gp55.

Figure 3:
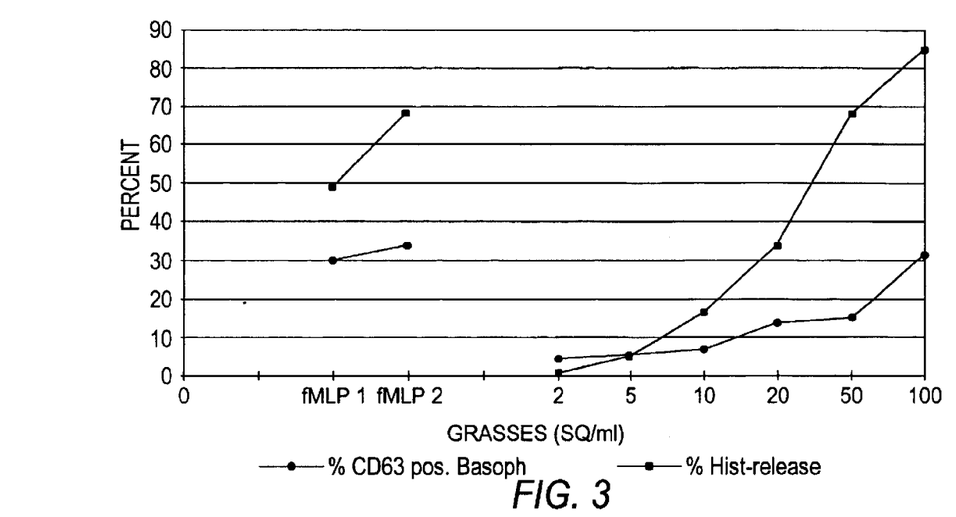
Figure 4:
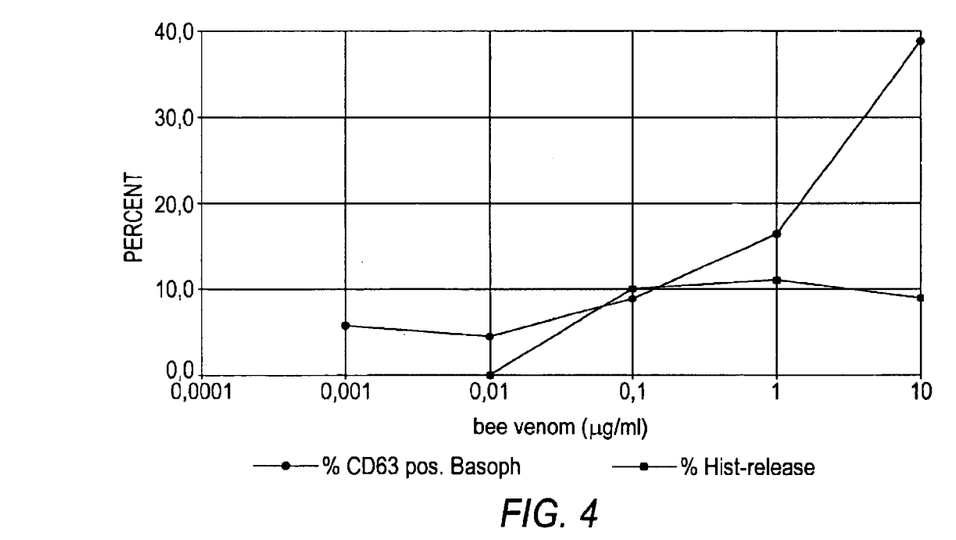
Figure 5:
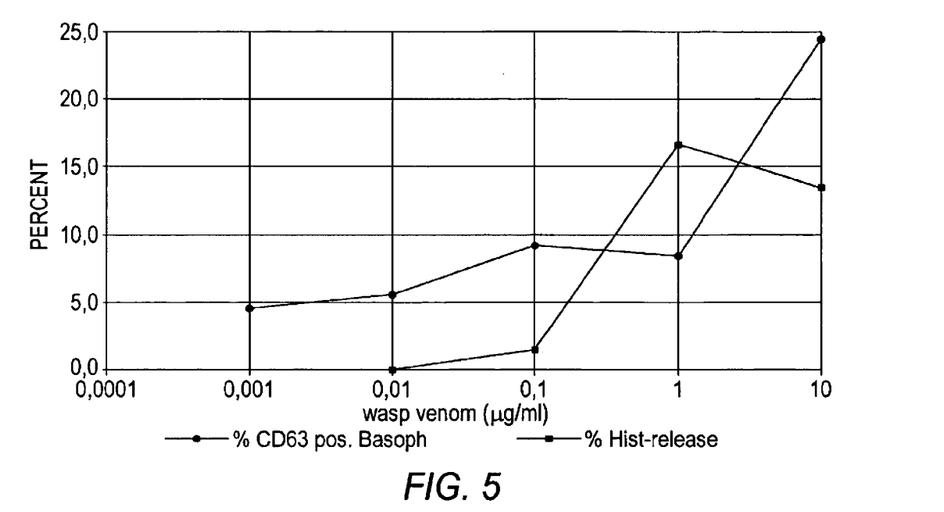
Figure 6:
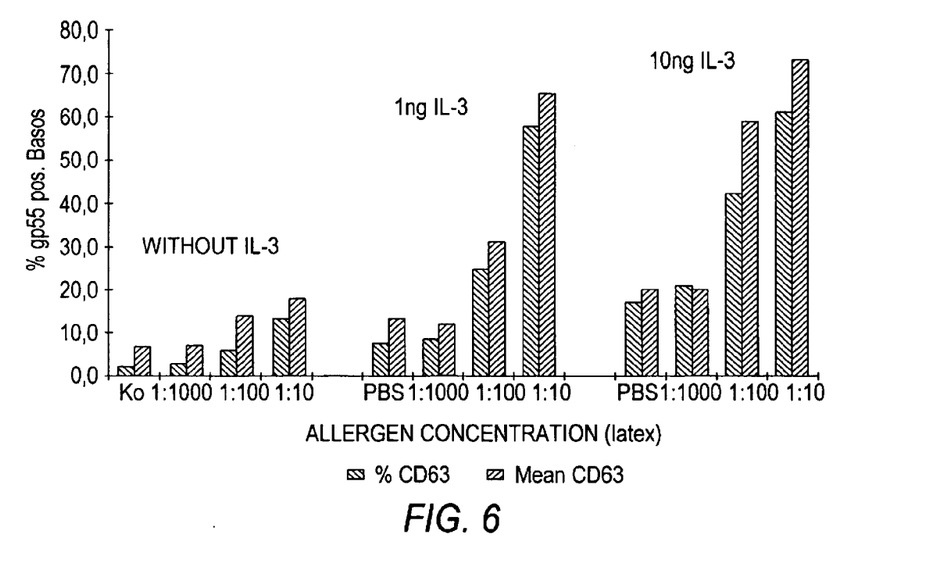
FIG. 6 shows that evaluation of a test according to the invention with prestiinulation with IL-3.

Results of the method according to the invention are shown in FIGS. 3–6. FIG. 3 shows a comparison of the method according to the invention (gp55 or CD63 expression) with a conventional histamine release test for the determination of a grass pollen allergy. Corresponding data are shown in FIG. 4 for the determination of a bee venom allergy and in FIG. 5 for the determination of a wasp venom allergy. An example of a latex allergen determination shown in FIG. 6 shows that the degranulation activity of basophils can be considerably increased by prestimulation with a cytokine like IL-3.

Legends

FSC=forward light scatter=narrow angle forward light scatter=cell size

SSC=side scatter=orthogonal light scatter=cell granularity algE-PE=IgE-PE=monoclonal antibody against immunoglobulin E, directly conjugated with the fluorescent dye phycoerythrin.

gp55-FITC=monoclonal antibody against the lysosomal glycoprotein with a molecular weight of 55 kD, directly conjugated with the fluorescent dye fluorescein.

CD45 cychrome=monoclonal antibody against the common cell surface glycoprotein of leukocytes directly conjugated with the tandem dye PE-cyanin 5.

R1, R2, R3=regions in which certain cells are located and which function as a logical gate. In this case they are the typical regions for basophilic granulocytes.

M1=marker region in which the cells which react positively to the antigen gp55 are located (degranulated basophils).

What is claimed is:

1. A method for the determination of degranulation activity of basophilic granulocytes in a whole blood sample, comprising:
    a) preincubating the whole blood sample with a stimulant that amplifies degranulation activity,
    b) incubating said whole blood sample with a test substance,
    c) incubating said whole blood sample witha first binding molecule which binds to either cell-bound IgE antibodies or to high affinity receptors thereof, and with a second binding molecule which binds to a CD63 molecule, wherein said first binding molecule and said second binding molecule (i) carry different marker groups which are detectable concurrently, or (ii) bind to different marker groups which are detectable concurrently, or (iii) one of said binding molecules carries a marker group and the other binds to a different marker group, said marker groups being detectable concurrently;
    d) lysing erythrocytes in said whole blood sample, and
    e) separately determining the marker groups of said first and second binding molecules, wherein degranulation activity in said whole blood sample is determined from the ratio between the cells that are positive for both the first and second binding molecule and the cells which are only positive for the first binding molecule.

2. The method of claim 1, wherein said stimulant is a cytokine.

3. The method of claim 2,wherein said cytokine is IL-3 or GM-CSF.

4. The method of claim 1, wherein at least one of said binding molecules is an antibody or an antibody fragment.

5. The method of claim 1, wherein said first binding molecule is an anti-IgE antibody, a fragment thereof, an anti-Fce$_e$RI antibody or a fragment thereof.

6. The method of claim 1, wherein said second binding molecule is an anti-CD63 antibody or a fragment thereof.

7. The method of claim 1, further comprising fixing leukocytes in said whole blood sample prior to separately determining said marker groups.

8. The method of claim 7, further comprising washing said whole blood sample after fixing leukocytes.

9. The method of claim 1, further comprising incubating the whole blood sample with a third binding molecule which binds to CD45 molecules, wherein said third binding molecule carries a marker group or binds to a marker group that is detectable separately from the marker group of the first and second binding molecules.

10. The method of claim 1, wherein said binding molecules are directly labeled.

11. The method of claim 1, wherein said binding molecules carry fluorescent markers.

12. The method of claim 11, comprising flow cytometry.

13. The method of claim 1, further comprising incubating said whole blood sample with a detectable DNA dye.

14. The method of claim 13, wherein said detectable DNA dye is a fluorescent dye.

15. The method of claim 14, wherein the fluorescent dye is 7-amino actinomycin D.

16. The method of claim 1, wherein said whole blood sample has been heparinized.

17. The method of claim 1, wherein said whole blood sample is a sample taken from a human.

18. The method of claim 1, comprising incubating said whole blood sample and test substance for 5–60 minutes at a temperature of 25–40° C.

19. The method of claim 18, comprising incubating for 20–40 minutes at a temperature of35–39° C.

20. The method of claim 1, comprising incubating said whole blood sample and said binding molecules for 10–40 minutes at a temperature of 0–10 ° C.

21. The method of claim 1, wherein second binding molecule is an anti-CD63 antibody, labeled with FITC.

22. The method of claim 1, wherein said sample is taken from a patient undergoing hyposensitization therapy.

23. Reagent kit useful in determination of degranulation activity of basophilic granulocytes, in whole blood, comprising (i) a first component which is a first binding molecule which binds to cell bound IgE antibodies or high affinity receptors thereof, (ii) a second component which is a second binding molecule which binds to a CD63 molecule, wherein said first and second binding molecules either carry different marker groups that are detectable concurrently or bind to different marker groups that are detectable concurrently, (iii) a third component which is a stimulant that amplifies degranulation activity of basophilic granulocytes, and (iv) a fourth component which is a reagent for lysing erythrocytes.

24. The reagent kit of claim 23, further comprising a third binding molecule which binds to a CD45 surface molecule and either carries a marker group which is detectable in addition to said markers of said first and second binding molecules or binds to said marker group.

25. The reagent kit of claim 23, further comprising a DNA dye.

26. The reagent kit of claim 23, further comprising a reagent for fixing leukocytes.

27. The reagent kit of claim 23, wherein said marker groups are flourescent labels.

28. The reagent kit of claim 23, wherein component (ii) is an anti-CD63-FITC antibody, or component (i) is an anti-IgE-PE antibody, or component (iv) is a FACS lysing solution, or the kit further comprises a test substance.

29. The reagent of kit of claim 23, further comprising at least one of 7-aminoactinomycin D, or an anti-CD45-PerCP antibody.

30. The reagent kit of claim 23, further comprising a buffer, an auxiliary substance or an additive.

31. A method for diagnosing allergic hypersensitivity in a patient comprising:
   (a) contacting a whole blood sample from said patient with (i) at least one allergen, (ii) a first binding molecule which binds to either cell-bound IgE antibodies or high affinity receptors thereof, and (iii) a second binding molecule which binds to a CD63 molecule, wherein said first and second binding molecules either carry different marker groups that are detectable concurrently or bind to different marker groups that are detectable concurrently,
   (b) determining said marker groups separately, and
   (c) comparing the values obtained with said allergen to the values obtained with a positive control and a negative control, wherein allergic hypersensitivity in said patient is indicated when the value obtained with said allergen is higher than the value obtained with the positive control.

32. A method for determining degranulation of basophilic granulocytes in a whole blood sample comprising contacting said sample with an antibody that binds to CD63 molecules, and determining binding of said antibody, wherein the level of binding is a measurement of degranulation of basic granulocytes in said sample.

33. A method for determining a patient's response to hyposensitization therapy comprising:
   (a) contacting a whole blood sample from said patient with (i) at least one allergen, (ii) a first binding molecule which binds to either cell-bound IgE antibodies or high affinity receptors thereof, and (iii) a second binding molecule which binds to a CD63 molecule, wherein said first and second binding molecules either carry different marker groups that are detectable concurrently or bind to different marker groups that are detectable concurrently,
   (b) determining said marker groups separately, and
   (c) comparing the values obtained with said allergen to the values obtained with a positive control and a negative control, wherein said patient has responded to hyposensitization therapy if the value obtained with said allergen is lower than the value obtained with the positive control.

* * * * *